United States Patent [19]

Mita et al.

[11] Patent Number: 4,675,439
[45] Date of Patent: Jun. 23, 1987

[54] PREPARATION PROCESS OF N-ACYLPHENYLALANINES

[75] Inventors: Ryuichi Mita; Toshio Katoh, both of Kawasaki; Chojiro Higuchi; Akihiro Yamaguchi, both of Kamakura, all of Japan

[73] Assignee: Mitsui Toatsu Chemicals, Incorporated, Tokyo, Japan

[21] Appl. No.: 794,562

[22] Filed: Nov. 4, 1985

Related U.S. Application Data

[63] Continuation-in-part of Ser. No. 800,066, Nov. 1, 1985, abandoned.

[30] Foreign Application Priority Data

Mar. 5, 1984 [JP] Japan ................... 59-40436
Jun. 7, 1984 [JP] Japan ................... 59-115431
Jun. 7, 1984 [JP] Japan ................... 58-115432
Jun. 7, 1984 [JP] Japan ................... 59-115433
Mar. 5, 1985 [WO] PCT Int'l Appl. ... .PCT/JP85/00109

[51] Int. Cl.$^4$ ............................................. C07C 99/00
[52] U.S. Cl. .................................. 562/443; 562/445; 562/446; 562/447; 562/450; 549/441
[58] Field of Search ............... 562/443, 445, 446, 447, 562/450, 576; 549/441

[56] References Cited

U.S. PATENT DOCUMENTS

| | | | |
|---|---|---|---|
| 3,010,992 | 11/1961 | Brathga et al. | 562/445 |
| 3,488,363 | 1/1970 | Hinkley | 562/446 |
| 3,517,057 | 6/1970 | Pines et al. | 562/446 |
| 3,804,894 | 4/1974 | Bernstein et al. | 562/447 |
| 4,261,919 | 4/1981 | Knowles et al. | 562/447 |
| 4,480,109 | 10/1984 | Ohashi et al. | 562/446 |

OTHER PUBLICATIONS

Fieser et al., "Reagents for Organic Synthesis", pp. 778–779 (1967).

*Primary Examiner*—James H. Reamer
*Attorney, Agent, or Firm*—Fisher, Christen & Sabol

[57] ABSTRACT

A process for preparing an N-acylphenylalanine represented by the formula (II):

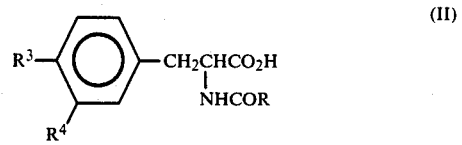

wherein $R_3$ and $R_4$ mean individually a hydrogen atom or an alkyl, alkoxy, phenoxy, hydroxy or methylenedioxy group, and R denotes a methyl or phenyl group, which comprises catalytically reducing an N-acyl-$\beta$-phenylserine represented by the formula (I):

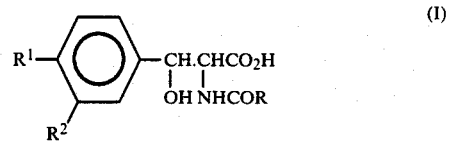

wherein $R_1$ and $R_2$ mean individually a hydrogen atom or an alkyl, alkoxy, phenoxy, benzyloxy or methylenedioxy group, and R has the same meaning as defined in the formula (II), in the presence of a reducing catalyst or both reducing catalyst and acid, in a solvent.

18 Claims, No Drawings

PREPARATION PROCESS OF N-ACYLPHENYLALANINES

This is a continuation-in-part of the U.S. national phase application Ser. No. 800,066, filed on Nov. 1, 1985, now abandoned, based on PCT/JP85/00109 (filed on March 5, 1985).

TECHNICAL FIELD

This invention relates to process for preparing an N-acylphenylalanin and more specifically to a process for preparing an N-acylphenylalanine by catalytically reducing its corresponding N-acyl$\beta$-phenyserine in the presence of a reducing catalyst in a solvent.

BACKGROUND ART

N-acylphenylalanines are important compounds as precursors for substituted or unsubstituted phenyl alanines. Especially, unsubstituted N-acylphenylalanine is a compound important as an intermediate for L-phenylalanine which has utility as a raw material for aspartame drawing attention as a low-calories artifical sweetener recently.

L-Phenylalanine may be prepared with ease, for example, by causing an enzyme, acylase, to act on N-actylphenylalanine.

As process for preparing an N-acylphenylalanine, it has conventionally been common to condense N-acetylglycine or N-benzoylglyine with a benzaldehyde to obtain 2-methyl (or phenyl)-4-benzylidene-5-oxazolone, to hydrolyze the oxazolone into its corresponding $\alpha$-acylaminocinnamic acid, and then to subject the cinnamic acid to catalytic reduction [for example, "Organic Synthesis", Coll. Vol. 2, P 1 and P 491 (1943) . The above process however results in the occurrence of various byproducts because the condensation reaction between N-acetylglycine or N-benzoylglycine and the benzaldehyde is effected in acetic anhydride, in the presence of sodium acetate, and with heating and under reflux. Accordingly, the above process is generally accompanied by such drawbacks that the resulting 2-methyl(or benzoyl)-4-benzylidene-5-oxazolone is poor in quality and low in yield. It has also been disclosed to prepare N-acetylphenylalanine from benzyl chloride, acetamide, carbon monoxide and hydrogen in the presence of a cobalt carbonyl catalyst (Japanese Patent Publication No. 37585/1982) or to prepare N-acetylphenylalanine by reacting styrene oxide, acetamide, carbon monoxide and hydrogen in the presence of a cobalt carbonyl/titanium isopropoxide catalyst (Japanese Patent Laid-open No. 85845/1983).

However, these processes involve problems such as limitations imposed on apparatus and the existence of potential danger since they are all reactions at high temperatures and elevated pressures.

DISCLOSURE OF THE INVENTION

The first object of this invention is to provide a novel process for the preparation of N-acylphenylalanines.

The second object of this invention is to provide a process capable of easily preparing N-acylphenylalanines with high yields.

By the present invention, the following process is provided for the preparation of an N-acylphenylalanine:

A process for preparing an N-acylphenylalanine represented by the formula (II):

wherein $R^3$ and $R^4$ are independently a hydrogen atom or a $C_1$–$C_4$ alkyl, $C_1$–$C_4$ alkoxy, phenoxy, hydroxy or methylenedioxy group, and R is a methyl or phenyl group, which comprises catalytically reducing an N-acyl-$\beta$-phenylserine represented by the formula (I):

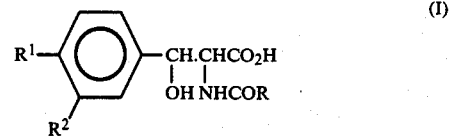

wherein $R_1$ and $R_2$ are independently a hydrogen atom or a $C_1$–$C_4$ alkyl, $C_1$–$C_4$ alkoxy, phenoxy, benzyloxy or methylenedioxy group, and R is a methyl or phenyl group, in the presence of a reducing catalyst in a solvent.

When the above catalytic reductipn is effected in the presence of a reducing catalyst and an acid and an alcohol is employed as a solvent in the present invention, an N-acylphenylalanine of the formula (II) can be obtained by treating the reducing reaction mixture with an aqueous alkaline solution.

BEST MODE FOR CARRYING OUT THE INVENTION

As N-acyl-$\beta$-phenylserines useful as raw materials in the process of this invention, may specifically be mentioned by way of example: N-acetyl-$\beta$-phenylserine, N-benzoyl-$\beta$-phenylserine, N-acetyl-$\beta$-(p-methylphenyl)serine, N-benzoyl-$\beta$-(p-methylphenyl)serine, N-acetyl-$\beta$-(p-ethylphenyl)serine, N-benzoyl-$\beta$-(p-ethylphenyl)serine, N-acetyl-$\beta$-(p-methoxyphenyl)serine, N-benzoyl-$\beta$-(p-methoxyphenyl)serine, N-acetyl-$\beta$-(m-phenoxyphenyl)serine, N-benzoyl-$\beta$-(m-methoxyphenyl)serine, N-acetyl-$\beta$-(3,4-dimethoxyphenyl)serine, N-benzoyl-$\beta$-(3,4-dimethoxyphenyl)serine, N-acetyl-$\beta$-(m-phenoxyphenyl)serine, N-benzoyl-$\beta$-(m-phenoxyphenyl)serine, N-acetyl-$\beta$-(p-benzyloxyphenyl)serine, N-benzoyl-$\beta$-(p-benzyloxyphenyl)serine, N-acetyl-$\beta$-lm-benzyloxyphenyl)serine, N-benzoyl-$\beta$-(m-benzyloxyphenyl)serine, N-benzoyl -$\beta$-(m-benzyloxyphenyl)serine, N-acetyl-$\beta$-(3,4-dibenzyloxyphenyl)serine, N-benzoyl-$\beta$-(3,4-dibenzyloxyphenyl)serine, N-acetyl-$\beta$-(3,4-methylenedioxyphenyl)serine, N-benzoyl-$\beta$-(3,4-methylenedioxyphenyl)serine, and so on. These compounds may be readily prepared by acylating $\beta$-phenylserines, which have been obtained by condensing glycine and benzaldehydes in the presence of an alkali and then treating the condensates with an acid, with acetic anhydride or benzoyl chloride by a usual method. Especially, $\beta$-phenylserines can be efficiently prepared by reacting glycine and benzaldehydes in two-layered systems, each, of water and a hydrophobic organic solvent (Japanese Patent Laid-open No. 32753/1985).

According to the process of this invention, N-acylphenylalanines can be obtained basically by catalytically reducing N-acyl-$\beta$-phenylserines of the formula (I) in state either suspended or dissolved in a solvent, in the presence of a reducing catalyst, and at either normal pressure or elevated pressure.

No particular limitation is imposed on the solvent to be employed, unless the solvent is by itself reduced upon the catalytic reduction. Usually, polar solvents having good miscibility with raw materials are used widely. As specific solvents, may be mentioned water; lower alcohols such as methanol, ethanol, n-propanol, isopropanol, n-butanol, isobutanol, tert-butanol, β-hydroxyethyl methyl ether and β-hydroxyethyl ethyl ether; ethers such as diethyl ether, dioxane, tetrahydrofuran and diethyleneglycol dialkyl ether; organic acids such as formic acid, acetic acid and propionic acid; ester-type solvents such as ethyl acetate, butyl acetate, triethyl phosphate and tributyl phosphate; nitrogen-containing solvents such as acetonitrile, pyridine, N,N-dimethylformamide, N,N-dimethylacetamide and N-methylpyrrolidone; sulfur-containing solvents such as sulforan and dimethylsulfoxide; and the like. Besides, solvents such as benzene, toluene, dichloromethane and dichloroethane may also be used. Two or more of these solvents may be used in combination. There is no specific limitation vested on the amount of the solvent to be employed. It may be used in any mount so long as the resultant reaction mixture can be stirred fully. Normally, the solvent may be used in an amount of 1–100 parts by weight or preferably 2–50 parts by weight, both based on each part by weight of the raw material, i.e., N-acyl-β-phenylserine.

The reducing catalyst useful in the practice of the process of this invention is a reducing catalyst of the heterogeneous system, such as palladium, platinum or rhodium with palladium being especially preferred. These catalysts are generally used in such forms as carried on various carriers. As such carriers, may be used a variety of carriers such as activated carbon, barium sulfate, alumina, silica and ferrite. Catalysts carrying palladium in amounts of 1–10 wt. % on these carriers are often employed. Needless to say, palladium black may also be used without developing any problems. The reducing catalyst may be employed in an amount of 0.3 wt. % or more, preferably in an amount of 0.5–30 wt. %, or more preferably in an amount of 1–20 wt. %, all based on the N-acyl-β-phenylserine.

The catalytic reduction in the present invention may be practiced under either normal pressure or an elevated pressure. When effecting the reaction under an elevated pressure, it is normally preferred to conduct the reaction under an elevated hydrogen pressure up to 30 kg/cm$^2$ in order to suppress a nucleus-hydrogenating reaction. On the other hand, the reaction temperature is in the range of 10°–120° C., preferably 20°–100° C., or more preferably 30°–80° C. If the reaction temperature should exceed 120° C., side reactions such as decompositions of raw materials and reaction product will occur. Therefore, such high reaction temperatures are not preferred.

By effecting the above-described catalytic reducing reaction in the presence of an acid in the present invention, the catalytic reduction of the N-acyl-β-phenylserine proceeds more smoothly and the yield of the N-acylphenylalanine is thus improved significantly. In this case, inorganic acids such as hydrochloric acid (hydrogen chloride), hydrobromic acid, sulfuric acid, perchloric acid and chlorosulfonic acid, aliphatic carboxylic or sulfonic acids such as trifluoroacetic acid, methanesulfonic acid and trifluoromethanesulfonic acid, and aromatic sulfonic acids such as benzenesulfonic acid, p-toluenesulfonic acid, xylenesulfonic acid, p-chlorobenzenesulfonic acid and naphthalnesulfonic acid may be used. When these acids are used, they are often employed singly but no problems will arise from the combined use of two or more acids. The acid may be used in an amount within the range of 0.05–4 equivalents or suitably 0.1–2 equivalents, both based on the raw material, N-acyl-β-phenylserine. If the acid is used in any amounts smaller than 0.05 equivalent, its addition give little effects to the reduction velocity. If the acid is added in any amounts greater than 4 equivalents, more byproducts are formed due to hydrolysis of the acyl groups in the N-acyl-β-phenylserine and N-acylphenylalanine and the yield of the N-acylphenylalanine is lowered. Therefore, it is not preferred to use the acid in any amounts outside the above range.

When preparing an N-acylphenylalanine of the formula (II) by the catalytic reduction of its corresponding N-acyl-β-phenylserine of the formula (I) in the concurrent presence of an acid, solvents employed for the reaction can be roughly divided into three types depending on the method for the isolation of the N-acylphenylalanine subsequent to the reaction.

Solvents of the first type are organic solvents and/or water. Suitable organic solvents are those capable of well-dissolving the starting N-acyl-β-phenylserine or the reduction product, i.e., N-acylphenylalanine and having good miscibility with water. As specific solvents, may be mentioned lower alcohols such as methanol, ethanol, n-propanol, isopropanol, tert-butanol, β-hydroxyethyl methyl ether and β-hyroxyethyl ethyl ether, ether-type solvents such as dioxane and tetrahydrofuran, carboxylic acids such as acetic acid and propionic acid, dimethylformamide, dimethylacetamide, N-methylpyrrolidone and so on. When the lower alcohols are employed out of these solvents, they are used as aqueous solutions containing 10 wt. % or more of water therein so as to retard the esterification reaction of a raw material and reaction product. When organic solvents other than alcohols are used as mixed solvents with water, there are no particular limitations on the ratios of water to such organic solvents.

Solvents of the second type are phosphoric acid triesters. Tributyl phosphate is particularly preferred. This solvent has large solubility to the raw material and reaction product and allows the catalytic reduction to proceed smoothly. Since it is an organic solvent immiscible with water, it has a merit that after the reaction, the isolation of the N-acylphenylalanine and the recovery of the solvent can be simplified as will be described herein.

Solvents of the third type are lower alcohols. As specific lower alcohols, may be mentioned methanol, ethanol, n-propanol, isopropanol, n-butanol, isobutanol, tert-butanol, β-hydroxyethyl methyl ether, β-hydroxyethyl ethyl ether and the like. When the catalytic reduction is effected in these solvents, the N-acylphenylalanine formed by the reaction has already been esterified either partly or mostly by the alcohols used as solvents although the esterification may depend on the type and amount of acid and the like. As will be described herein, the reaction mixture of catalytic reduction is therefore treated with an aqueous alkaline solution for its hydrolysis so that the esterified N-acylphenylalanine is converted to free N-acylphenylalanine.

The isolation of the resulting N-acylphenylalanine is carried out in the following manner.

In the case of a solvent of the first type, the following procedure may be followed for the isolation of the resultant N-acylphenylalanine from the reaction mixture subsequent to the catalytic reduction. Namely where the reaction product is in a dissolved state subsequent to the reaction, the N-acylphenylalanine may be isolated by filtering off the reducing catalyst, adding an aqueous alkaline solution to neutralize the acid, distilling off the organic solvent under reduced pressure and then treating the residue with water and a mineral acid such a hydrochloric acid. When the reaction has been carried out in water or in a mixed solvent of water and an organic solvent, the N-acylphenylalanine is often in a crystalline form after the reaction. Accordingly, the N-acylphenylalanine can be precipitated by adding an aqueous alkaline solution subsequent to the reaction to dissolve the N-acylphenylalanine, filtering off the catalyst, driving off the solvent and then adding a mineral acid such as hydrochloric acid.

In the case of a solvent of the second type, the isolation of the N-acylphenylalanine may be effected in the following manner subsequent to the catalytic reduction. Where the reaction product is in a dissolved form after the reaction, the N-acylphenylalanine can be precipitated by filtering off the reducing catalyst to obtain a filtrate, extracting the N-acylphenylalanine from the filtrate with an aqueous alkaline solution, for example, an aqueous solution of sodium hydroxide in an amount at least equal to the total of the amount equivalent to the strong acid used in the reaction and the amount equivalent to the starting N-acyl-β-phenylserine, allowing the resultant mixture into separate layers, adding a mineral acid such as hydrochloric acid to the water layer to acidify the same. Where the produced N-acylphenylalanine has been crystallized out partly or mostly as a precipitate subsequent to the reaction, it is only necessary to collect the N-acylphenylalanine together with the reducing catalyst, to dissolve the filtered mass with an aqueous alkaline solution such as an aqueous solution of sodium hydroxide so as to separate the N-acylphenylalanine solution from the catalyst, to extract and separate the N-acylphenylalanine dissolved in the filtrate with an aqueous alkaline solution, to combine the solution and extract, and then to add an acid to the combined solution for the crystallization of the N-acylphenylalanine.

Where an organic solvent immiscible with water such as the above-mentioned tributyl phosphate is employed, the solvent which is recovered subsequent to the extraction and separation of the N-acylphenyl alanine with the aqueous alkaline solution can be recirculated for its reuse after merely washed with water without need for its further purification by distillation.

In the case of a solvent of the third type, the N-acylphenylalanine formed by the reaction has already been esterified either partly or mostly with the alcohol employed as the solvent although the esterification may vary depending on the type and amount of the used acid and the like. In order to convert the thus-esterified N-acylphenylalanine to the free N-acylphenylalanine, the reaction mixture of the reduction is treated with an aqueous alkaline solution. This treatment may be effected after the reducing reaction, by adding the aqueous alkaline solution to the solution obtained by filtering off the reducing catalyst or by adding the aqueous alkaline solution prior to filtering off the reducing catalyst. As the aqueous alkaline solution employed in the above treatment, aqueous solutions of alkali metal hydroxides are often used. It may however be possible to use the hydroxide or oxide of an alkaline earth metal in a state suspended in water. As specific examples of the aqueous alkaline solution, may be mentioned aqueous solutions and suspensions of sodium hydroxide, potassium hydroxide, lithium hydroxide, calcium hydroxide, calcium oxide, barium hydroxide and barium oxide. It is necessary to use the aqueous alkaline solution in an amount at least equal to the total of the amount required to neutralize the acid employed for the catalytic reduction and the amount equivalent to the starting N-acyl-β-phenylserine. On the other hand, the temperature and time of the treatment with the aqueous alkaline solution may respectively be 20°–100° C. and 0.5–5 hours or preferably 30°–80° C. and 1–3 hours. Under these conditions, the ester is hydrolyzed to form the free N-acylphenylalanine. The thus-prepared N-acylphenylalanine may be isolated as crystals if the alcohol solvent is distilled off under reduced pressure from the solution treated with the aqueous alkaline solution and the resultant mixture is then acidified with a mineral acid such as hydrochloric acid or sulfuric acid for the precipitation of the N-acylphenylalanine.

In the manner mentioned above, the process of this invention can prepare with good efficiency the N-acylphenylalanine which corresponds to the N-acyl-β-phenylserine employed as the raw material. However, where the raw material is a benzyloxy-substituted N-acyl-β-phenylserine, the benzyloxy group is also reduced and a hydroxy-substituted N-acylphenylalanine is obtained.

As has been described above, the process of this invention is a process having a high value as an industrial preparation process because it is a preparation process having various merits such that (1) the starting N-acyl-β-phenylserines are compounds which can be easily prepared from glycine and benzaldehydes by way of β-phenylserines; (2) the catalytic reductions of the N-acyl-β-phenylserines proceed smoothly under mild conditions especially when an acid is present, thereby preparing the N-acylphenylalanines with high yields; and (3) the reaction procedure and the like are simple.

This invention will hereinafter be described in detail by the following Examples.

In the following Examples, the following analytical conditions were employed for high-performance liquid chromatography.

Column:
YMC-Pack A-312, 6 mm across×150 mm (packing material: ODS).

Mobile phase:
0.005 M/liter aqueous solution of sodium heptanesulfonate:methanol=6:4 (by volume) ... adjusted to pH 2 with phosphoric acid.

Flow velocity:
1.0 ml/mm.

Detector:
Ultraviolet spectrophotometer (wavelength: 225 nm).

EXAMPLE 1

Charged in a hermetically-sealed 100-ml glass vessel were 5.6 g of N-acetyl-β-phenylserine, 30 ml of isopropanol and 0.22 g of 5% palladium/carbon. After nitrogen sweep, catalytic reduction was carried out at 40°–45° C., for 8 hours and at normal pressure.

After the reaction, the catalyst was filtered off and the filtrate was analyzed by high-performance chromatography. As a result, the filtrate was found to contain 0.16 g of N-acetylphenylalanine. This is equivalent to an yield of 3.1 mole % based on the raw material, i.e., N-acetyl-β-phenylserine.

EXAMPLES 2-5

Catalytic reductions were conducted in the same manner as in Example 1 except that 5.6 g of N-acetyl-β-phenylserine was used and the catalyst, solvent and hydrogen pressure were varied. Results are shown in Table 1.

TABLE 1

| Ex. No. | Catalyst Type | Amount (g) | Solvent Type | Amount (ml) | Reaction time & hour (°C./hr.) | Yield of N—acetyl-phenylalanine* (mole %) | Reaction pressure |
|---|---|---|---|---|---|---|---|
| 2 | 5% Pd/carbon | 0.22 | Water | 30 | 50–65/8 | 8.3 | normal |
| 3 | 5% Pd/barium sulfate | 0.22 | Acetic acid | 35 | 50–60/8 | 8.1 | " |
| 4 | 5% Pt/carbon | 0.2 | Acetic acid | 35 | 45–50/8 | 7.3 | " |
| 5 | 5% Pd/carbon | 0.11 | 90% Ethanol | 30 | 55–60/4 | 6.7 | 20 kg/cm$^2$ |

*Analysis data by high-performance liquid chromatography.

EXAMPLE 6

Suspended in 30 ml of water was 5.6 g of N-acetyl-β-phenylserine, followed by addition and dissolution of 2.2 g of 45% sodium hydroxide. The resultant aqueous solution was charged in a 300-ml autoclave and after sweeping it with nitrogen, hydrogen was charged under pressure to a hydrogen pressure of 20 kg/cm$^2$. Thereafter, the temperature was raised to 50° C. and its catalytic reduction was effected at 50°–55° C. for 5 hours. After exhausting hydrogen from the autoclave and sweeping the autoclave with nitrogen subsequent to the reaction, the catalyst was filtered off and the filtrate was analyzed by high-performance liquid chromatography. As a result, it was found that N-acetylphenylalanine was prepared with a yield of 7.2 mole %.

EXAMPLE 7

Following the procedure of Example 6 except that 6.73 g of N-benzoyl-β-phenylserine was used in place of the N-acetyl-β-phenylserine and the amount of water increased to 50 ml, N-benzoylphenylalanine was prepared with a yield of 6.8 mole %.

EXAMPLE 8

To a hermetically-sealed 100-ml glass vessel, were charged 5.6 g of N-acetyl-β-phenylserine, 50 ml of dioxane, 0.28 g of 5% palladium/carbon and 1.2 g of p-toluenesulfonic acid monohydrate. After the interior of the vessel was swept with nitrogen and then with hydrogen, a catalytic reduction was carried out at 50°–52° C. for 9 hours. During this period, hydrogen absorption reaching about 95% of the stoichiometric amount was recognized. After the reaction, the vessel was cooled to room temperature and purged with nitrogen. Then, the catalyst was filtered off and washed with a small amount of dioxane. The filtrate and washing were combined. Results of an analysis on the combined solution were as follows:

N-Acetylphenylalanine:
  92.5 mole % (based on N-acetyl-β-phenylserine)
N-Acetyl-β-phenylserine:
  1.8 mole % (based on N-acetyl-β-phenylserine)
β-Phenylserine:
  1.5 mole % (based on N-acetyl-β-phenylserine)
Phenylalanine:
  1.3 mole % (based on N-acetyl-β-phenylserine)

After adding 2.5 g of a 10% aqueous solution of sodium hydroxide to the solution, the dioxane solvent was distilled off under reduced pressure. After adding 20 ml of water and 1.0 g of 35% hydrochloric acid to the residue and stirring the mixture thoroughly, the mixture was filtered at 5° C., washed with chilled water and then dried, thereby obtaining 4.40 g of white N-acetylphenylalanine.
Purity: 100%
Melting point: 150°–151° C.
Yield: 84.9%

EXAMPLE 9

In a hermetically-sealed 100-ml glass vessel, were charged 5.6 g of N-acetyl-β-phenylserine, 50 ml of water, 0.28 g of 5% palladium/carbon and 1.2 g of 98% sulfuric acid. After the interior of the vessel was swept with nitrogen and then with hydrogen, a catalytic reduction was carried out at 60°–65° C. for 20 hours. During this period, hydrogen absorption reaching about 70% of the stoichiometric amount was recognized. After the reaction, the vessel was cooled down to room temperature and purged with nitrogen. Then, 45% sodium hydroxide was added to adjust the pH to 8. The catalyst was filtered off and washed with a small amount of water. The filtrate and washing were combined. Results of an analysis on the combined solution were as follows:

N-Acetylphenylalanine:
  62.4 mole % (based on N-acetyl-β-phenylserine)
N-Acetyl-β-phenylserine:
  15.3 mole % (based on N-acetyl-β-phenylserine)
Phenylalanine: 6.8 mole % (based on N-acetyl-β-phenylserine)
β-Phenylserine: 14.9 mole % (based on N-acetyl-β-phenylserine)

EXAMPLE 10

A catalytic reduction was carried out in exactly the same manner in Example 8 except that 50 g of tetrahydrofuran was used in lieu of the dioxane and 1.2 g of methanesulfonic acid was used instead of p-toluenesulfonic acid. Hydrogen absorption of about 95% of the stoichiometric amount was recognized at 50°–52° C. in 9 hours. After the reaction, the vessel was cooled down to room temperature and swept with nitrogen. Then, the catalyst was filtered off and washed with a small amount of tetrahydrofuran. The filtrate and washingswere combined, and the resultant solution was analyzed. The following results were obtained.

N-Acetylphenylalanine:
  91.7 mole % (based on N-acetyl-β-phenylserine)
N-Acetyl-β-phenylserine:
  2.6 mole % (based on N-acetyl-β-phenylserine)

β-Phenylserine:
1.3 mole % (based on N-acetyl-β-phenylserine)
Phenylalanine:
1.6 mole % (based on N-acetyl-β-phenylserine)

N-acetylphenylalanine was isolated from the reaction solution in the same manner as in Example 8. As a result, N-acetylphenylalanine was obtained with an yield of 4.43 g and a melting point of 150°–151° C.

EXAMPLE 11

A catalytic reaction was carried out in the same manner as in Example 8 except that 1.43 g of trifluoroacetic acid was used in place of the p-toluenesulfonic acid. Hydrogen absorption reaching about 95% of the stoichiometric amount was observed at 50°–52° C. in 8 hours. After the reaction, the vessel was swept with nitrogen and the catalyst was filtered off and washed with a small amount of dioxane. The filtrate and washing were combined and the resultant solution was analyzed. The following result were obtained.
N-Acetylphenylalanine:
90.8 mole % (based on N-acetyl-β-phenylserine)
N-Acetyl-β-phenylserine:
4.3 mole % (based on N-acetyl-β-phenylserine)
β-Phenylserine:
2.1 mole % (based on N-acetyl-β-phenylserine)
Phenylalanine:
1.9 mole % (based on N-acetyl-β-phenylserine)

EXAMPLE 21

The reaction, namely, the catalytic reduction of Example 8 was conducted under the condition of a hydrogen pressure of 5 kg/cm$^2$, at 50° C. and for 8 hours, using a glass-made autoclave. The following results were obtained.
N-Acetylphenylalanine:
94.9 mole % (based on N-acetyl-β-phenylserine)
N-Acetyl-β-phenylserine:
0.3 mole % (based on N-acetyl-β-phenylserine)
Phenylalanine:
0.7 mole % (based on N-acetyl-β-phenylserine)
β-Phenylserine:
1.3 mole % (based on N-acetyl-β-phenylserine)

EXAMPLE 13

Charged in a hermetically-sealed 200-ml glass vessel were 7.88 g of N-acetyl-β-(m-phenoxyphenyl)-serine, 80 g of dioxane, 0.3 g of 5% palladium/carbon (50% water-containing product) and 1.2 g of p-toluenesulfonic acid monohydrate. A catalytic reduction was then conducted at 50°–55° C. and normal pressure, in the same manner as in Example 8. In 10 hours, hydrogen absorption reaching about 95% of the stoichiometric amount was recognized. After the reaction, the catalyst was filtered off and the solution was analyzed by high-performance liquid chromatography. As a result, the yield of N-acetyl-(m-phenoxyphenyl)alanine was found to be 92.9 mole % [based on N-acetyl-β-(m-phenoxyphenyl)serine]. By treating the solution in the same manner as in Example 8, 6.7 g of N-acetyl-(m-phenoxyphenyl)alanine was obtained. Melting point: 145°–146° C.

EXAMPLE 14

Charged in a hermetically-sealed 100-ml glass vessel were 5.60 g of N-acetyl-β-phenylserine and 50 ml of tributyl phosphate, followed by further addition of 0.28 g of 5% palladium/carbon and 1.2 g of p-toluenesulfonic acid monohydrate. After sweeping the interior of the reaction vessel with nitrogen and then with hydrogen, a reduction was conducted under normal pressure, at 50°–60° C. and for 15 hours. During this period, hydrogen absorption of substantially the stoichiometric amount (molar ratio: 1) was recognized.

After purging at the same temperature with nitrogen subsequent to the reaction, the catalyst was filtered off and washed with a small amount of tributyl phosphate. The filtrate and washings were combined. Thirty grams of a 5% aqueous solution of sodium hydroxide were added to the resultant solution to extract the latter. After allowing the resultant mixture to stand, the water layer and solvent layer were separated. The solvent layer was again extracted with 20 ml of a 1% aqueous solution of sodium hydroxide. The aqueous extract layers were combined.

The aqueous solution was analyzed by high-performance liquid chromatography. As a result, the yield of N-acetylphenylalanine was found to be 96.2 mole % (based on N-acetyl-β-phenylserine). On the other hand, the percent remainder of the raw material, namely, N-acetyl-β-phenylserine was 0.8 mole %. The yields of β-phenylserine and phenylalanine as byproducts were 0.7 mole % and 1.4 mole % respectively.

After adding concentrated hydrochloric acid to the aqueous solution at 20°–25° C. to adjust its pH to 1, the aqueous solution was cooled to 0°–5° C. and the deposited crystals were collected by filtration. By washing the crystals with chilled water and then drying them, 4.54 g of white N-acetylphenylalanine was obtained.
Melting point: 150°–151° C.
Purity: 99.8%
Yield: 87.6 mole % (based on N-acetyl-β-phenylserine)

EXAMPLES 15–21

Reactions were conducted using 5.6 g of N-acetyl-β-phenylserine and changing the amount of tributyl phosphate, the type and amount of the reducing catalyst and the type and amount of the strong acid. Results are shown in Table 2. The analysis data were obtained by extracting filtrates, which had been obtained by filtering off the catalysts after the reactions, with an aqueous solution of sodium hydroxide and then analyzing the separated water layers in the same manner as in Example 14.

TABLE 2

| Ex. No. | Tributyl phosphate (ml) | Catalyst Type | Amount (g) | Strong acid Type | Amount (g) |
|---|---|---|---|---|---|
| 15 | 50 | 5% Pd/C | 0.11 | 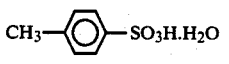 | 3.6 |
| 16 | 40 | 5% Pd/C | 0.28 | CF$_3$CO$_2$H | 1.43 |
| 17 | 40 | 5% Pd/BaSO$_4$ | 0.28 | 98% H$_2$SO$_4$ | 1.25 |
| 18 | 40 | 5% P/C | 0.56 | ClSO$_3$H | 1.46 |
| 19 | 40 | 5% P/C | 0.28 | 35% HCl | 2.0 |

TABLE 2-continued

| | | | | | |
|---|---|---|---|---|---|
| 20 | 40 | 5% P/C | 0.28 | CH₃SO₃H | 0.72 |
| 21 | 40 | 5% P/C | 0.28 | 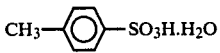 CH₃—◯—SO₃H.H₂O | 1.25 |

| | Reducing conditions | | Results (mole % N—acetyl-β-phenylserine) | | | |
|---|---|---|---|---|---|---|
| Ex. No. | H₂ pressure (kg/cm²) | °C./hr | N—Acetyl-phenylalanine | N—acetyl-β-phenylserine | Phenylalanine | β-Phenylserine |
| 15 | Normal | 50–55/15 | 93.6 | 0.5 | 2.9 | 2.4 |
| 16 | Normal | 50–55/10 | 92.3 | 4.9 | 1.5 | 0.6 |
| 17 | Normal | 50–60/15 | 89.3 | 3.4 | 3.1 | 2.8 |
| 18 | Normal | 50–60/15 | 88.5 | 4.1 | 3.0 | 3.6 |
| 19 | Normal | 50–60/12 | 88.4 | 5.3 | 2.6 | 3.4 |
| 20 | Normal | 55–60/12 | 96.3 | 1.7 | 1.3 | 0.7 |
| 21 | 5 | 40–50/8 | 95.1 | 2.31 | 1.1 | 0.6 |

EXAMPLE 22

Charged in a hermetically-sealed 100-ml glass vessel were 7.13 g of N-benzoyl-β-phenylserine and 60 ml of tributyl phosphate, followed by further addition of 0.28 g of 5% palladium/carbon and 2.4 g of p-toluenesulfonic acid monohydrate. After sweeping the interior of the reaction vessel with nitrogen and then with hydrogen, a reduction was conducted under normal pressure, at 55°–60° C. and for 15 hours. During this period, hydrogen absorption of about 95% of the stoichiometric amount was recognized.

After purging at the same temperature with nitrogen subsequent to the reaction, the catalyst was filtered off and washed with a small amount of tributyl phosphate. The filtrate and washing were combined. Fifty grams of a 5% sodium hydroxide were added to the resultant solution to extract the latter. After allowing the resultant mixture to stand, the water layer and solvent layer were separated. The solvent layer was again extracted with 30 ml of a 1% aqueous solution of sodium hydroxide. The aqueous extract layers were combined and analyzed by high-performance liquid chromatography. The following results were obtained.
N-Benzoylphenylalanine:
  92.8 mole % (based on N-benzoyl-β-phenylserine)
N-Benzoyl-β-phenylserine:
  3.9 mole % (based on N-benzoyl-β-phenylserine)
Phenylalanine
  1.7 mole % (based on N-benzoyl-β-phenylserine)
β-Phenylserine:
  1.4 mole % (based on N-benzoyl-β-phenylserine)

Concentrated hydrochloric acid was added at 20°–25° C. to the water layer until its pH reached 1. After cooling the solution to 5° C., the deposited crystals were collected by filtration, washed with chilled water and then dried to obtain 6.00 g of white N-benzoylphenylalanine.
Melting point: 185°–186.5° C.
Purity: 99.6%
Yield: 88.8%

EXAMPLE 23

After charging 7.88 g of N-acetyl-β-(m-phenoxyphenyl)serine, 70 ml of tributyl phosphate, 0.39 g of 5% palladium/carbon and 2.4 g of p-toluenesulfonic acid monohydrate in a hermetically-sealed 100-ml glass vessel, a catalytic reduction was conducted normal pressure in the same manner as in Example 14. Hydrogen absorption of substantially the stoichiometric amount was recognized at 50°–60° C. in 15 hours.

A water layer, which had been obtained by extracting with an aqueous solution of sodium hydroxide, was analyzed in the same manner as in Example 14. As a result, the yield of N-acetyl-m-phenoxyphenylalanine was found to be 94.5%. By treating the water layer with an acid, 6.7 g of N-acetyl-m-phenoxyphenylalanine was obtained as white crystals having a melting point of 145°–146° C. Yield: 89.6%.

EXAMPLE 24

Charged in a hermetically-sealed 100-ml glass vessel were 5.6 g of N-acetyl-β-phenylserine, 50 g of methanol, 1.23 g of 98% concentrated sulfuric acid and 0.56 g of 5% palladium/carbon (50% water-containing product).

After sweeping the interior of the reaction vessel with nitrogen and then with hydrogen, a reduction was conducted at normal pressure, at 50°–55° C. and for 12 hours. During this period, hydrogen absorption reaching 95% of the theoretical value was recognized. After cooling the reaction vessel to 30° C. and purging it with nitrogen subsequent to the reaction, the palladium/carbon catalyst was filtered off and washed with a small amount of methanol. The filtrate and washing were combined. Fifty grams of a 5% aqueous solution of sodium hydroxide were added to the solution and the resultant mixture was stirred at 30°–35° C. for 2 hours. Thereafter, the methanol was distilled off under reduced pressure and the resulting aqueous solution was analyzed by high-performance liquid chromatography. As a result, the yield of N-acetylphenylalanine was found to be 87.1 mole % (based on N-acetyl-β-phenylserine) whereas the percent remainder of the material, starting N-acetyl-8-phenylserine was determined to be 4.1 mole %. The extents of the byproduction of phenylalanine and β-phenylserine which were both obtained by hydrolyzing the acetyl group were 5.6 mole % and 3.2 mole % (both based of N-acetyl-β-phenylserine).

After adding concentrated hydrochloric acid to the aqueous solution at 30° C. to adjust its pH to 1, the aqueous solution was cooled to 5° C. and the deposited crystals were collected by filtration. By washing the crystals with a small amount of chilled water and then drying the same, 4.3 g of N-acetylphenylalanine was obtained as white crystals.
Melting point: 150°–151° C.
Purity: 100%

EXAMPLES 25-29

Similar to Example 24, catalytic reductions were conducted using 5.6 g of N-acetyl-β-phenylserine and changing the type of the alcohol solvent, the type and amount of the reducing catalyst, the type of the acid and the like. Thereafter, the reaction mixtures were treated with an aqueous sodium hydroxide to conduct the analysis of N-acetylphenylalanine. Results are shown in Table 3.

Melting point: 186°-187° C.
Purity: 99.8%
Yield: 81.8%

EXAMPLE 31

A reaction was effected in the same manner as in Example 24 except that 7.88 g of N-acetyl-β-(m-phenoxyphenyl)serine was used in place of the N-acetyl-β-phenylserine.

Hydrogen absorption reaching about 95% of the stoichiometric amount was recognized at 50°-55° C. in 12 hours.

After the reduction, the reaction mixture was also treated with an aqueous sodium hydroxide solution in the same manner as in Example 24. An aqueous solution which had been obtained by distilling off the solvent was analyzed by high-performance liquid chromatography. As a result, the yield of N-acetyl-m-phenoxyphenylalanine was found to be 87.6%. By treating the resultant aqueous solution with hydrochloric acid, 6.3 g of N-acetyl-m-phenoxyphenylalanine was obtained as white crystal having a melting point of 145°-146° C. Yield: 84.2%.

TABLE 3

| Ex. No. | Alcohol Type | Amount (g) | Catalyst Type | Amount (g) | Acid Type | Amount (g) |
|---|---|---|---|---|---|---|
| 25 | Methanol | 50 | 5% Pd/C (50% water-containing product) | 0.22 | 98% H$_2$SO$_4$ | 1.23 |
| 26 | Methanol | 50 | 5% Pd/C (50% water-containing product) | 0.56 | CH$_3$SO$_3$H | 1.20 |
| 27 | Isopropanol | 50 | 5% Pd/BaSO$_4$ | 0.28 | CH$_3$—⌬—SO$_3$H.H$_2$O  | 2.4 |
| 28 | β-Hydroxyethyl methyl ether | 50 | 5% Pd/C | 0.28 | CH$_3$—⌬—SO$_3$H.H$_2$O  | 2.4 |
| 29 | Methanol | 50 | 5% Pd/C | 0.28 | CH$_3$—⌬—SO$_3$H.H$_2$O  | 2.4 |

| | Reducing conditions | | Results (mole % N—acetyl-β-phenylserine*) | | | |
|---|---|---|---|---|---|---|
| Ex. No. | H$_2$ pressure (Kg/cm$^2$) | °C./hr | N—Acetylphenylalanine | N—acetyl-β-phenylserine | Phenylalanine | β-phenylserine |
| 25 | Normal | 40-50/18 | 86.4 | 4.5 | 5.2 | 3.5 |
| 26 | Normal | 50-55/12 | 88.3 | 3.6 | 4.5 | 2.9 |
| 27 | Normal | 50-55/15 | 84.8 | 5.3 | 5.3 | 3.6 |
| 28 | Normal | 50-55/15 | 85.6 | 4.2 | 5.1 | 4.7 |
| 29 | 5 | 45-50/10 | 89.2 | 2.7 | 3.8 | 3.4 |

*After each reducing reaction, the catalyst was filtered off, 50 g of a 5% aqueous solution of sodium hydroxide was added, and the resultant mixture was stirred at 30-35° C. for 1-2 hours to hydrolyze the ester which had been formed upon the reduction. Thereafter, the solvent, i.e., the alcohol was distilled off under reduced pressure and the resultant aqueous solution was analyzed by high-performance liquid chromatography.

EXAMPLE 30

A catalytic reduction was conducted in exactly the same manner as in Example 24 except that 7.13 g of N-benzoyl-β-phenylserine was used in place of the N-acetyl-β-phenylserine. After the reaction, the catalyst was filtered off and washed with a small amount of methanol. The filtrate and washing were combined, and 50 g of a 5% sodium hydroxide was added to the resultant solution, followed by a reaction at 30°-35° C. for 1 hour. Thereafter, the methanol was distilled off under reduced pressure and the thus obtained aqueous solution was analyzed by high-performance liquid chromatography. The following results were obtained.

N-Benzoylphenylalanine:
  85.9 mole % (based on N-benzoyl-β-phenylserine)
N-Benzoyl-β-phenylserine:
  5.6 mole % (based on N-benzoyl-β-phenylserine)
Phenylalanine:
  4.1 mole % (based on N-benzoyl-β-phenylserine)
β-Phenylserine:
  4.0 mole % (based on N-benzoyl-β-phenylserine)

Concentrated hydrochloric acid was added at 30° C. to the aqueous solution to lower its pH to 1. After cooling the solution to 5° C., the deposited crystals were collected by filtration, washed with a small amount of chilled water and then dried to obtain 5.15 g of N-benzoylphenylalanine as white crystals.

EXAMPLE 32

Charged in a hermetically-sealed 300 ml glass vessel were 80 g of n-butanol, 0.55 g (0.0055 mole) of 98% concentrated sulfuric acid, 22.3 g (0.1 mole) of N-acetyl-β-phenylserine and b 0.67 g of 5% palladium/carbon.

After sweeping the interior of the reaction vessel with nitrogen and then with hydrogen, a catalytic reduction was conducted at normal pressure at 80° C. and for 8 hours. During this period, hydrogen absorption reaching 95% of the theoretical value was recognized. After cooling the reaction vessel to 40° and purging it with nitrogen subsequent to the reaction, the catalyst was filtered off and washed with 20 g of n-butanol. The filtrate and washings were combined. 120 ml of water and 14.8 g of a 45% aqueous solution of sodium hydroxide were added to the combined solution. The resultant mixture was stirred at 30°–35° C. for 2 hours. Thereafter, the n-butanol was distilled off under reduced pressure and the resulting aqueous solution was analyzed by high-performance liquid chromatography.
Results are as follows:
N-Acetylphenylalanine:
  87.8 mole % (based on N-acetyl-β-phenylserine)
N-Acetyl-β-phenylserine:
  1.3 mole % (based on N-acetyl-β-phenylserine)
-Phenylserine:
  3.5 mole % (based on N-acetyl-β-phenylserine)
Phenylalanine:
  5.9 mole % (based on N-acetyl-β-phenylserine)

EXAMPLE 33

A reaction was conducted in the same manner as in Example 25 except that 2.1 g of p-toluenesulfonic acid monohydrate in place of the 98% concentrated sulfuric acid. As a result, the conversion of N-acetyl-β-phenylserine into was 85.5 mole %.

What is claimed is:
1. Process for preparing an N-acylphenylaline represeted by the formula II:

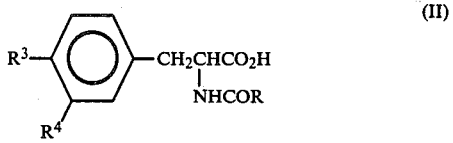

wherein $R_3$ and $R_4$ each are a hydrogen atom or an alkyl, alkoxy, phenoxy or hydroxy group or $R_3$ and $R_4$ together are a methylenedioxy group, and R is a methyl or phenyl group, comprises catalytically reducing with hydrogen an N-acyl-β-phenyl-serine represented by the formula (I):

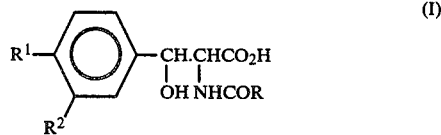

wherein $R_1$ and $R_2$ each are a hydrogen atom or an alkyl, alkoxy, phenoxy or benzyloxy group or $R_1$ and $R_2$ together are a methylenedioxy group, and R has the same meaning as defined in the formula (II), in a solvent selected from the group consisting of water, at least one organic solvent, and a mixed solvent of water and at least one organic solvent, in the presence of a reducing catalyst selected from the group consisting of palladium, platinum and rhodium, and in the presence of a strong acid selected from the group consisting of an inorganic acid, an aliphatic sulfonic acid, an aromatic sulfonic acid and trifluoroacetic acid, at a temperature of 10° to 120° C.

2. A process according to claim 1, wherein the reducing catalyst is palladium.

3. A process according to claim 1, wherein the acid is an inorganic acid.

4. A process according to claim 1, wherein the acid is an aliphatic sulfonic acid.

5. A process according to claim 1, wherein the acid is an aromatic sulfonic acid.

6. The process according to claim 1 wherein the organic acid is trifluoroacetic acid.

7. A process according to claim 1, wherein the solvent is a phosphoric acid triester.

8. A process according to claim 1, wherein the solvent is a lower alcohol.

9. The process according to claim 1 wherein after the catalytic reduction, the reaction mixture is treated with an aqueous alkaline solution to obtain the N-acylphenylalanine.

10. The process according to claim 1 wherein the organic solvent is dioxane or tetrahydrofuran.

11. The process according to claim 7 wherein the phosphoric triester is selected from the group consisting of triethyl phosphate and tributyl phosphate.

12. The process according to claim 8 wherein the lower alcohol is selected from the group consisting of methoanol, ethanol, n-propanol, isopropanol, n-butanol, isobutanol, tert-butanol, β-hydroxyethyl methyl ether and β-hydroxyethyl ether.

13. The process according to claim 1 wherein the acid is sulfuric acid, hydrochloric acid or chlorosulfonic acid.

14. The process according to claim 1 wherein the acid is methanesulfonic acid or trifluoromethanesulfonic acid.

15. The process according to claim 1 wherein the acid is selected from the group consisting of benzenesulfonic acid, p-toluenesulfonic acid, xylenesulfonic acid and naphthalenesulfonic acid.

16. The process according to claim 1 wherein the acid is present in an amount within the range of 0.05 to 4 equivalents based on the N-acyl-β-phenyl serine.

17. The process according to claim 1 wherein the reaction temperature is 30° to 80° C.

18. The process according to claim 1 wherein the reaction pressure is atmospheric pressure or an elevated hydrogen pressure up to 30 kg/cm².

* * * * *